(12) United States Patent
Törnsten et al.

(10) Patent No.: US 12,390,597 B2
(45) Date of Patent: *Aug. 19, 2025

(54) TRACK-INDEXED SYRINGE

(71) Applicant: GALDERMA HOLDING SA, Zug (CH)

(72) Inventors: Jonas Törnsten, Uppsala (SE); Max Blomqvist, Uppsala (SE); Pekka Niskala, Torshälla (SE)

(73) Assignee: Galderma Holding SA, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/434,351

(22) Filed: Feb. 6, 2024

(65) Prior Publication Data
US 2024/0181164 A1    Jun. 6, 2024

Related U.S. Application Data

(63) Continuation of application No. 17/979,589, filed on Nov. 2, 2022, now Pat. No. 11,896,806, which is a (Continued)

(30) Foreign Application Priority Data

Mar. 28, 2013 (EP) .................. 13161533

(51) Int. Cl.
*A61M 5/31* (2006.01)
*A61M 5/315* (2006.01)

(52) U.S. Cl.
CPC ........ *A61M 5/3137* (2013.01); *A61M 5/3159* (2013.01); *A61M 5/31595* (2013.01); (Continued)

(58) Field of Classification Search
CPC ........ A61M 5/3137; A61M 2005/3139; A61M 5/3159
See application file for complete search history.

(56) References Cited

U.S. PATENT DOCUMENTS 4,710,179 A * 12/1987 Haber ............... A61M 5/31595
604/211
4,915,695 A    4/1990 Koobs
(Continued)

FOREIGN PATENT DOCUMENTS

CH        293302 A  *  9/1953
JP     2011-510727 A      4/2011
(Continued)

OTHER PUBLICATIONS

English translation of Eisenhut (CH 293302) (Year: 1953).*
(Continued)

*Primary Examiner* — Courtney B Frederickson
(74) *Attorney, Agent, or Firm* — Sunit Talapatra; Foley & Lardner LLP

(57) ABSTRACT

The present invention relates to a finger grip (1) arranged to be connected to a syringe barrel having a plunger and a plunger rod for driving said plunger. The finger grip comprises a body having a lower side with finger supporting surfaces (13) for supporting fingers of a user during handling and an engagement member (5) being moveable between an inactive position where the engagement member is arranged not to engage with the plunger rod of the syringe barrel and an active position where the engagement member is arranged to engage with a grooved surface on the plunger rod of the syringe such that feedback is given to a user as the plunger is moved relative to the finger grip. An activation member (7) for moving the engagement member from said inactive position to said active position is built-in into the finger grip.

20 Claims, 5 Drawing Sheets

Related U.S. Application Data continuation of application No. 16/888,110, filed on May 29, 2020, now Pat. No. 11,504,479, which is a continuation of application No. 14/780,888, filed as application No. PCT/EP2014/056298 on Mar. 28, 2014, now Pat. No. 10,668,219.

(52) U.S. Cl.
CPC ... *A61M 2005/3139* (2013.01); *A61M 5/3148* (2013.01); *A61M 2205/581* (2013.01); *A61M 2205/582* (2013.01)

(56) References Cited

U.S. PATENT DOCUMENTS

| | | | | |
|---|---|---|---|---|
| 2007/0265579 | A1* | 11/2007 | Kleyman | ............ A61C 5/62 604/207 |
| 2011/0009829 | A1 | 1/2011 | Kosinski et al. | |

FOREIGN PATENT DOCUMENTS

| | | |
|---|---|---|
| WO | WO-03/015845 A3 | 2/2003 |
| WO | WO-2008/016381 A1 | 2/2008 |
| WO | WO-2008/057976 A2 | 5/2008 |
| WO | WO-2009/095735 | 8/2009 |

OTHER PUBLICATIONS

International Search Report issued on International Application No. PCT/EP2014/056298 dated Jun. 4, 2014 (5 pages).
Written Opinion issued on International Application No. PCT/EP2014/056298 dated Jun. 4, 2014 (6 pages).

* cited by examiner

TRACK-INDEXED SYRINGE

CROSS-REFERENCE TO RELATED APPLICATIONS

The present application is a continuation application of U.S. application Ser. No. 17/979,589 filed Nov. 2, 2022, which is a continuation application of U.S. application Ser. No. 16/888,110 filed May 29, 2020, now U.S. Pat. No. 11,504,479, which application is a continuation application of U.S. application Ser. No. 14/780,888 filed Sep. 28, 2015, now U.S. Pat. No. 10,668,219, which is the national stage entry of PCT/EP2014/056298 filed Mar. 28, 2014, which claims priority to European Patent Application No. 13161533.8 filed Mar. 28, 2013. The benefit of priority to these prior-filed applications is hereby claimed and the entire contents of these applications are incorporated herein by reference.

FIELD OF THE INVENTION

The present invention relates to syringes, and more particularly to a finger grip for a syringe.

BACKGROUND OF THE INVENTION

When a user of a medical syringe administers a substance, it is common, in particular within certain areas of treatment, to distribute the total volume carried by the syringe over an area. Some examples of such areas of treatment are dermatology, plastic surgery, cosmetic surgery, and odontology. The distribution is for instance done by inserting the needle of the syringe just beneath and approximately in parallel with the skin surface and then administering the substance while withdrawing the needle. Another way is to administer the substance at several anatomic locations within a limited area, i.e. to administer a fraction of the total volume at each location. In both these, and other, methods of distributing the substance it is an advantage if the syringe is provided with some kind of dosing aid, which aids the user in knowing how large fraction of the total volume of the substance is administered at each location or per time unit. Conventionally, the syringe barrel is provided with a gradation scale, and the user observes the position of the plunger along the scale. However, the scale is difficult to see and might be partly or fully covered by a sticker, or the like, and the syringe is at times held at an angle where the scale is hidden. Further, a main problem with the use of a gradation scale as such is the fact that a user has to observe it during injection which means that a distraction of attention arises when the user has to look at the gradation scale every now and then instead of focusing on the course of events at the treatment area. Mechanic or electronic injectors providing an accurate dosing have been used, but they are more expensive and heavier than syringes and many users prefer to hold the injection device in the way that a conventional syringe is held. Further, most injectors do not allow a user to perform needle aspiration prior to injection of the medicament. This is a serious drawback since it does not allow a user to realize that injection has been done in a blood vessel.

An effort to provide a syringe with a dosing aid is disclosed in WO 2008/057976, and in WO 2008/016381, where an engagement member is provided on the finger grip is movable between an inactive, or non-engaging, position and an active position where it engages with a structure of the plunger rod. However, in WO 2008/057976 it is unclear how the movement is actually realized due to a most schematic illustration and description thereof.

In WO 2008/016381 the operation of moving the engagement member between the two positions is uncomfortable due to the structure providing for that operation.

SUMMARY OF THE INVENTION

It would be advantageous to provide a syringe with user firendly means that informs and provides feedback to a user about the injected amount or an injection rate.

To better address this concern, in a first aspect of the invention there is presented a finger grip arranged to be connected to a syringe barrel having a proximal and a distal end and having a plunger and a plunger rod for driving said plunger, said finger grip comprising a body having a lower side which, when mounted to a syringe barrel, faces towards said proximal end of the syringe barrel and an oppositely facing upper side, wherein finger supporting surfaces for supporting fingers of a user during handling are provided on said lower side. The finger grip further comprising an engagement member being moveable radially of the plunger rod between an inactive position where the engagement member is arranged not to engage with the plunger rod of the syringe barrel and an active position where the engagement member is arranged to engage with a grooved surface on the plunger rod such that tactile and sound feedback is given to a user as the plunger is moved relative to the finger grip. An activation member, operable axially of the plunger rod for moving the engagement member from the inactive position to the active position is built-in into the finger grip. The built-in activation member provides a safer, more hygienic and more convenient solution than the prior art solution lacking an activation member. The provision of an engagement member is also convenient during needle aspiration. The engagement member will give an unambiguous indication that the plunger rod actually has been retracted a certain distance such that structural flexibility can be excluded, which might otherwise give a false indication during needle aspiration. I.e. the user believes that the needle aspiration indicates that injection will not be performed into a blood vessel whereas the plunger has in reality not yet been moved due to flexibility of the system. The provision of an engagement member according to the invention can eliminate, or at least reduce, this drawback.

In accordance with an embodiment of the finger grip, the activation member is arranged to move the engagement member from said active position to said inactive position. Thereby it is possible to easily switch both from the inactive position to the active position and from the active position to the inactive position.

In accordance with an embodiment of the finger grip, the activation member is accessible from the upper side of the finger grip. Thereby the activation member is readily operable when the user holds a syringe provided with the finger grip, for example by using the thumb of the hand holding the syringe.

In accordance with an embodiment of the finger grip, the body comprises a frame portion extending around an outer perimeter of the finger grip and the activation member is received within said frame portion. Thereby it is possible to minimize the height of the finger grip, and the frame portion prevents unintentional operation of the activation member from the side of the finger grip.

In accordance with an embodiment of the finger grip, an inner surface of the frame portion and an outer surface of the activation member comprise mating connecting members for securing the activation member to the body. Thereby the operation of assembling the finger grip is facilitated.

In accordance with an embodiment of the finger grip, the activation member comprises a fixed part attached to the body and a moving part for moving the engagement member, wherein the fixed part and the moving part are joined to each other by a pivoting joint.

In accordance with an embodiment of the finger grip, a return stop is provided between the frame portion and the engagement member for preventing the activation member from moving the engagement member from said active position to said inactive position. In some applications it is an advantage to be able to ensure that the engagement member is kept in the active position.

In accordance with an embodiment of the finger grip, the fixed part of the activation member and the body comprise concentric openings through which a plunger rod of a syringe can pass.

In accordance with an embodiment of the finger grip, an upper surface of the activation member is flush with an upper surface of the frame portion when the engagement member is in said inactive position. Thereby the risk of unintentional activation is reduced.

In accordance with an embodiment of the finger grip, an upper surface of the activation member is depressed relative the upper surface of the frame portion when the engagement member has been moved to the active position. Thereby it is easier to determine that the active position is taken.

In accordance with an embodiment of the finger grip, the engagement member comprises a biasing member biasing the engagement member towards said inactive position. Thereby the engagement member does not have to be connected with the activation member in order to switch the engagement member from the active to the inactive position when the activation member is moved.

In accordance with another aspect of the present invention, there is provided a medical syringe comprising a barrel for containing a medicament, and a plunger rod for driving the plunger. The plunger rod is provided with grooves extending circumferentially of the plunger rod, and the medical syringe further comprises a finger grip as described above.

These and other aspects, and advantages of the invention will be apparent from and elucidated with reference to the embodiments described hereinafter.

BRIEF DESCRIPTION OF THE DRAWINGS

The invention will now be described in more detail and with reference to the appended drawings in which.

DESCRIPTION OF PREFERRED EMBODIMENTS

Figure 1:
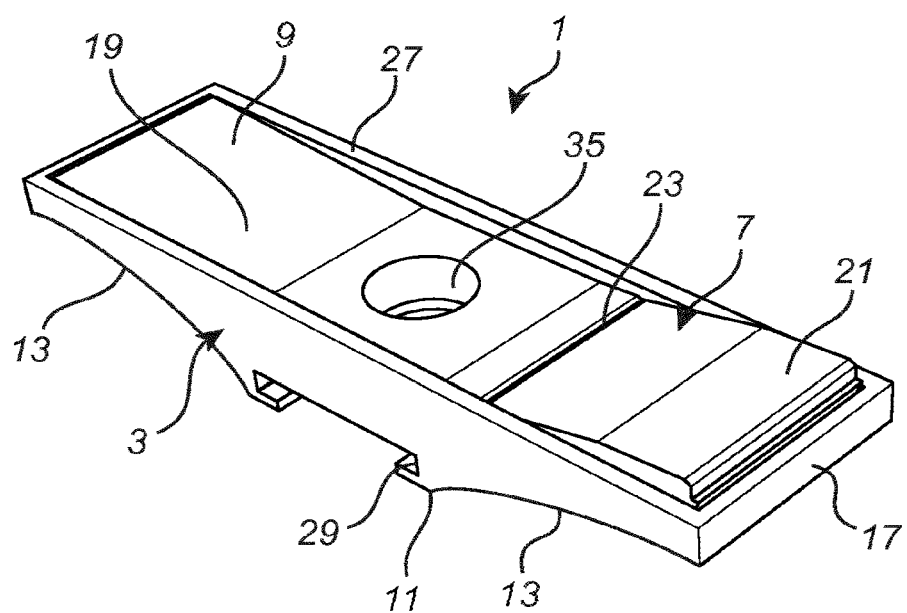
FIG. 1 is a perspective view of an embodiment of a finger grip according to the present invention.
Figure 2:
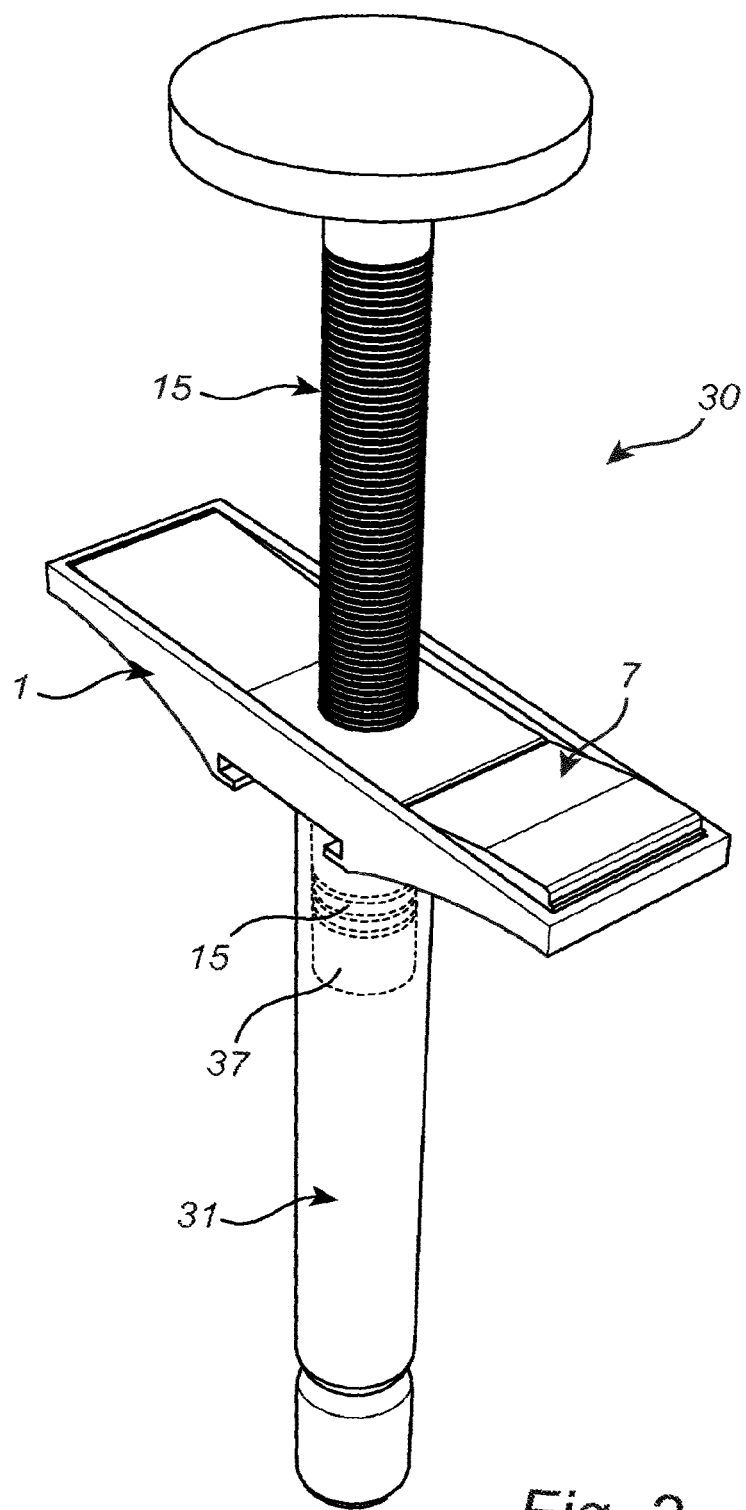
FIG. 2 is a perspective view of a syringe including the finger grip of FIG. 1.
Figure 3:
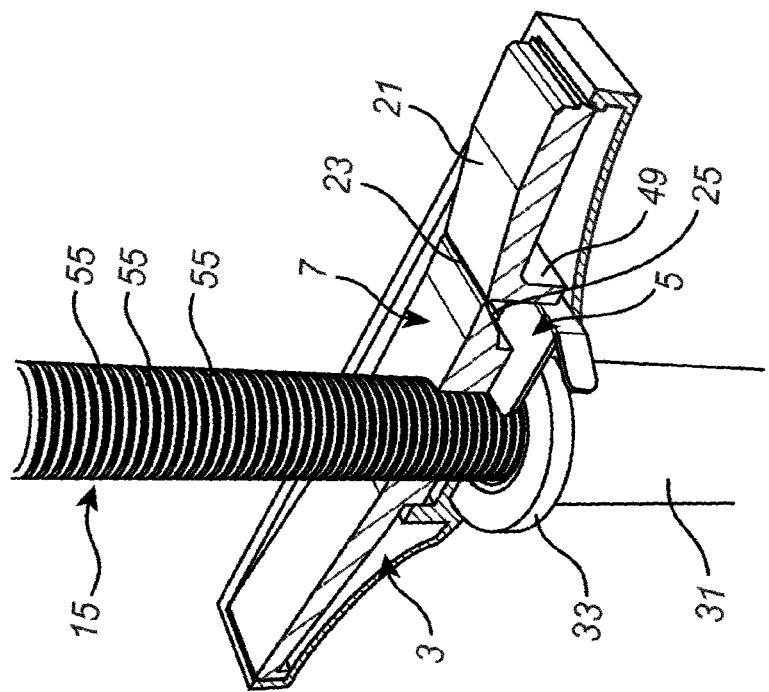
FIG. 3 is a perspective and partly sectional view of a part of the syringe of FIG. 2.

An embodiment of the finger grip 1, as most schematically illustrated in FIG. 1, comprises a body 3, an engagement member 5, which is hidden within the finger grip 1 as shown in FIG. 3, and an activation member 7. The body 3 and the activation member 7 are typically manufactured from a thermoplastic such as polyolefin, polyamide or polycarbonate. These examples are, of course, only a small number of examples of suitable plastics and the skilled person realizes that there are many other suitable materials in addition to these. The engagement member 5 typically is made of metal but it is very well imaginable that it could be made of plastics as well. It is possible to manufacture the engagement member by injection moulding together with other parts of the finger grip. The finger grip 1 has an upper, or distal, side 9, and a lower, or proximal, side 11. Finger supporting surfaces 13 are provided at the lower side 11 for supporting fingers of a user during handling. The engagement member 5 is arranged to engage with a plunger rod 15, see FIG. 2 showing a syringe 30 including the finger grip 1, though lacking a needle, and is movable radially of the plunger rod 15, by means of the activation member 7, between an inactive, or rear, position in which it does not engage with the plunger rod 15 and an active, or front, position in which it does engage with the plunger rod 15, as will be further described below. The activation member 7 is accessible from the upper side 9 of the finger grip 1.

Figure 7:
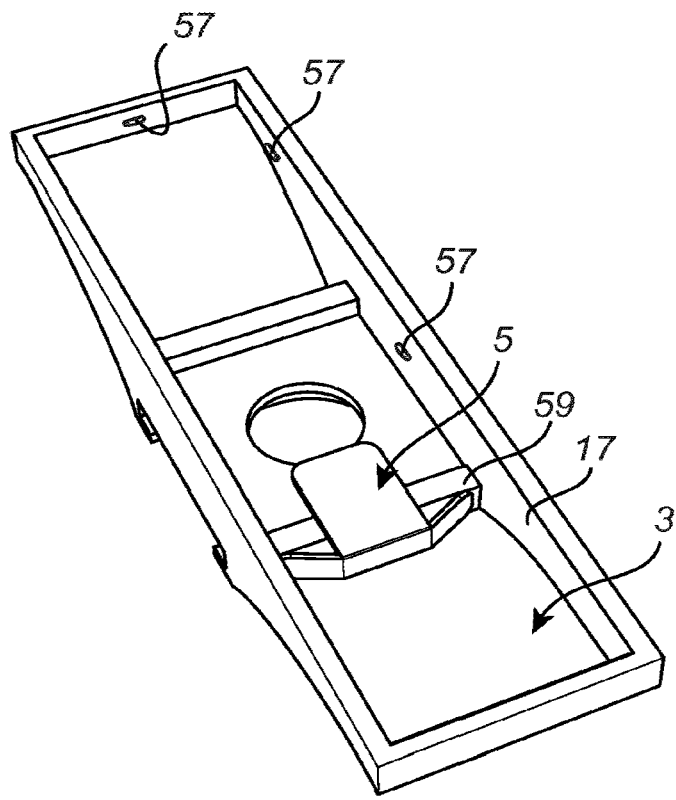
FIG. 7 is a perspective view of a part of the finger grip of FIG. 1.

The body 3 comprises a frame portion 17, which extends around an outer perimeter of the finger grip 1, and the activation member 7 has been received within the frame portion 17. The activation member 7 is plate shaped and has a fixed part 19, which is rigidly engaged with the frame portion 17, and which is a major part of the activation member 7. The fixed part 19 of the activation member 7 is provided with engagement means (not shown in the figures) along an outer perimeter thereof that correspond to engagement means 57 provided along an inner surface of the frame portion 17, shown in FIG. 7 such that the activation member 7 can be held within the frame portion 17 by means of a snap-fit. During assembly of the finger grip 1, the activation member 7 is simply pressed down into the frame portion 17 so that it snaps into an assembled position. Thus, the frame portion 17 and an outer surface of the activation member 7 have mating connection members. They can be realized as optional combinations of protrusions or protrusions and recesses. Furthermore, the activation member 7 has a moving part 21 for moving the engagement member 5. The fixed part 19 is joined with the moving part 21 by a pivotable joint 23. The joint 23 is provided as a narrow portion extending across the activation member 7 and being thinner than the adjacent portions of the activation member 7 by a V-shaped groove 25 at the underside of the activation member 7. This creates a hinge in the plastic material that is used for manufacturing the activation member 7. In the figures, the moving part 21 is shown to extend above an upper surface of frame portion 17 when the engagement member 5 is in the in-active position and to assume a position where an upper surface thereof is flush with an upper surface of frame portion 17 when the engagement member 5 is in the active position, i.e. when moving part 21 is depressed. It is of course also possible within the scope of the present invention to imagine embodiments where the upper surface of the moving part 21 is flush with the upper surface of frame portion 17 when the engagement member 5 is in the inactive position, and where the upper surface of the moving part 21 is depressed relative to the upper surface of the frame portion 17 in the active position of the engagement member 5. Both versions provide immediate tactile and visual feedback to a user as to the current position of the engagement member, providing the finger grip of the present invention with a major advantage over prior art solutions where it might be necessary to move the plunger rod in order to determine the position of the engagement member.

The body 3 is provided with a generally semi-circular recess 29, arranged to receive a end flange 33 of a barrel 31 being a part of the syringe 30, as shown in FIG. 2, such that the end flange 33 of barrel 31 will be received and held within recess 29 with a press-fit or a snap-fit. The activation member 7 is provided with a hole 35, arranged to receive the plunger rod 15 of the syringe 30. The hole 35 is concentric with the recess 29.

The medical syringe 30 is assembled as follows. The finger grip 1 is mounted at a distal end of the barrel 31 as described above, and the plunger rod 15 is inserted into the barrel 31 down through the hole 35 of the activation member and is connected with a plunger 37, for instance by means of matching threads on the proximal end of the plunger rod 15 and the plunger 37, inside of the barrel 31. The provision of a threaded connection between the plunger rod 15 and the plunger 37 has a further advantage in that it allows a user to perform needle aspiration prior to injection. Other types of plunger-plunger rod connections may only allow movement of the plunger in one direction, i.e. pushing it through the barrel 31 towards a proximal end thereof, thus rendering needle aspiration impossible.

Figure 4:
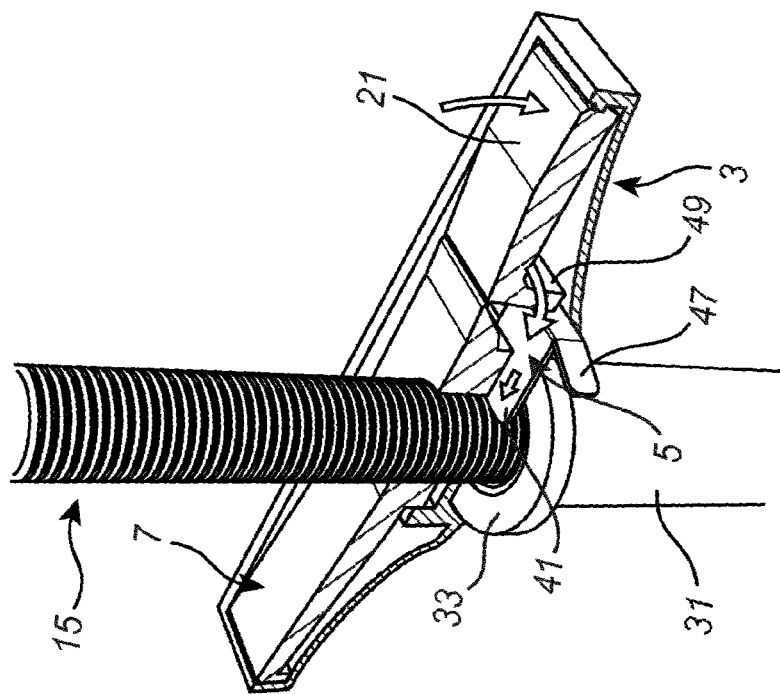
FIG. 4 is a perspective and partly sectional view of a part of the syringe of FIG. 2.
Figure 5:
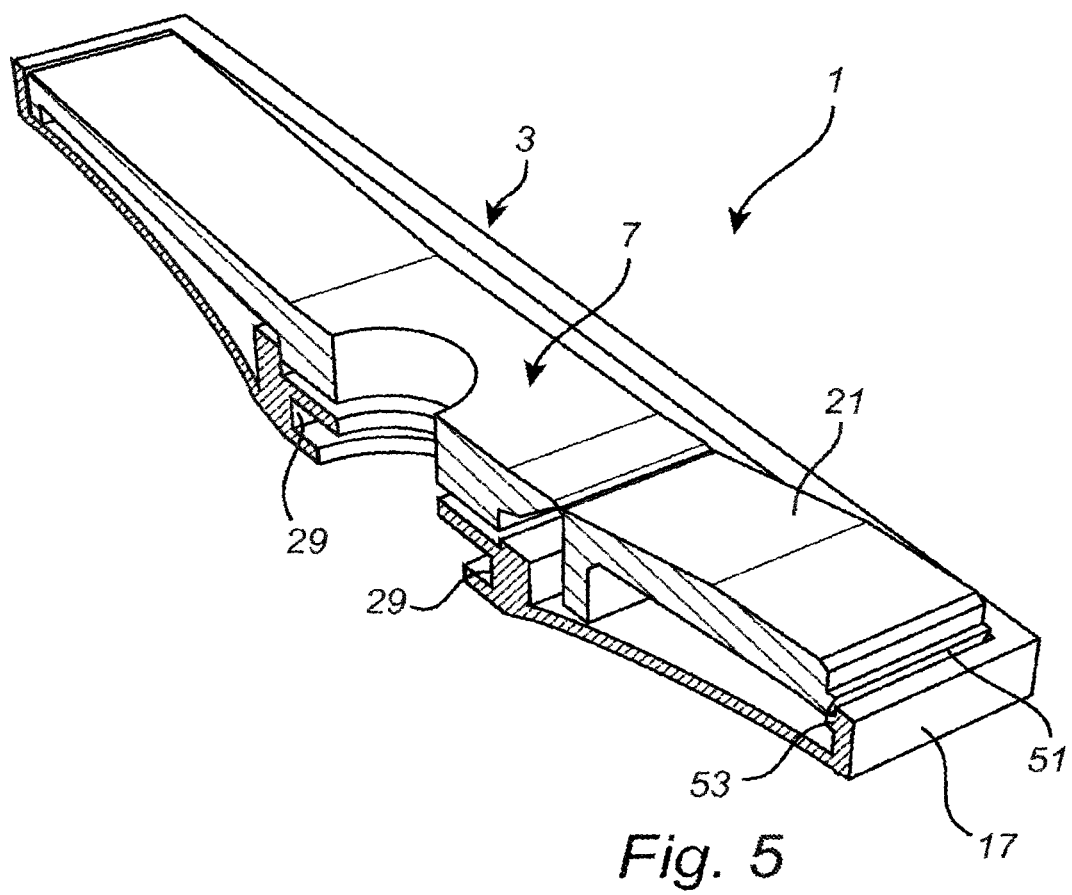
FIG. 5 is a sectional view of a part of the finger grip of FIG. 1.
Figure 6:
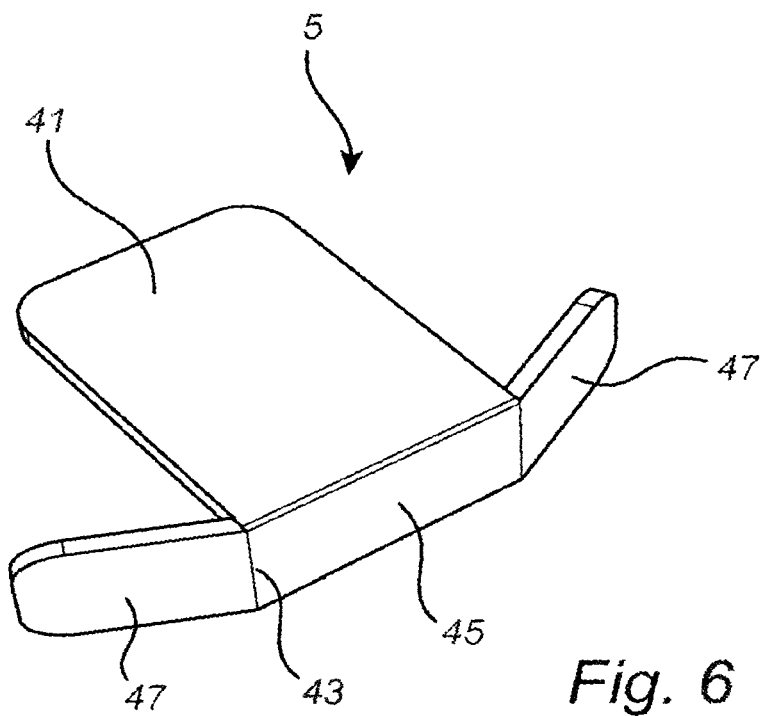
FIG. 6 is a perspective view of a part of the finger grip of FIG. 1.

The engagement member 5 is made of a sheet metal and comprises an engagement portion 41, which is arranged to engage with the plunger rod 15, and a spring portion 43, constituting a biasing member arranged to bias the engagement member 5 away from the plunger rod 15. The engagement portion 41 is plate shaped and extends perpendicular to a longitudinal centre axis of the plunger rod 15, i.e. radially of the plunger rod 15, and along the length of the finger grip 1. The spring portion 43 is plate shaped and comprises a centre portion 45 extending perpendicular to the engagement portion 41, and two wings 47 at each end of the centre portion 45, extending obliquely forwards, i.e. towards the plunger rod 15. The free ends of the wings 47 abut against a fixed abutment portion 59 of the body 3. The moving portion 21 of the activation member 7 comprises a pusher portion 49 protruding at an underside of the activation member 7 and abutting against the centre portion 45 of the spring portion 43. The activation member 7 is operable axially of, though of course in parallel with, the plunger rod 15 between the inactive position and the active position, i.e. it can be pushed down and pushed up again, the pushing being performed in the direction of the longitudinal centre axis. This is more convenient for the user, and is a safer operation, than to move the engagement member directly in the radial direction as described in the prior art. When the activation member 7 is pushed down it pivots around joint 23 thereby moving the engagement member from an inactive position, see FIG. 3, where it does not engage with the plunger rod 15, to an active position, see FIG. 4, where it does engage with the plunger rod 15. During the movement to the active position, a protrusion 51 at the free end of the moving portion 21 engages with a corresponding protrusion 53 at an inner wall of the frame 17, see FIG. 5. The protrusions 51, 53 embody a snap-in lock which retains the moving portion 21 and thus keeps the engagement member 5 in the active position.

The plunger rod 15 is provided with a large number of narrow grooves, defined by narrow flanges 55. The pitch of the flanges 55, i.e. the centre distance between two adjacent flanges, is for instance between 0, 1 and 2 mm. The pitch is typically chosen depending on the substance to be injected and the size, i.e. the diameter, of the barrel of the syringe. A narrow barrel means that a smaller amount is expelled from the syringe for a given travel of the plunger and accordingly a larger pitch of the flanges could be used representing a certain amount of injected substance. Further, the plunger rod could preferably be carried out as a hollow rod. The plunger rod 15 would typically be manufactured by injection moulding and if the plunger rod 15 is made solid, cooling of the product would be rather time consuming in order to avoid problems with shrinkage which in turn would cause tolerance problems of the flanges, i.e. varying distances between flanges 55 and varying protrusion of the flanges 55. Such tolerance variations are of course unwanted and often not tolerable. Therefore, the plunger rod 15 could be made hollow which saves material and remedies the cooling and tolerance problems. The plunger rod 15 may optionally be provided with different pitches along different parts thereof. This would make a single plunger rod suitable for different needs, substances and desires of different users. To switch between the different pitches, a user simply rotates the plunger rod until a flanges having a preferred pitch is positioned facing the engagement member. When the engagement member 5 is in the active position, and the user is administering the medical substance, and thus pushes the plunger rod 15 further into the barrel 31, a sound is generated by the flanges 55 passing the engagement member 5, which gives feedback to the user. It is easy for the user to learn to associate the sound with the amount of medical substance that is administered, and also to associate the sound with a certain injection rate, thereby allowing the user to accurately dose the substance and distribute it as desired.

Figure 8:
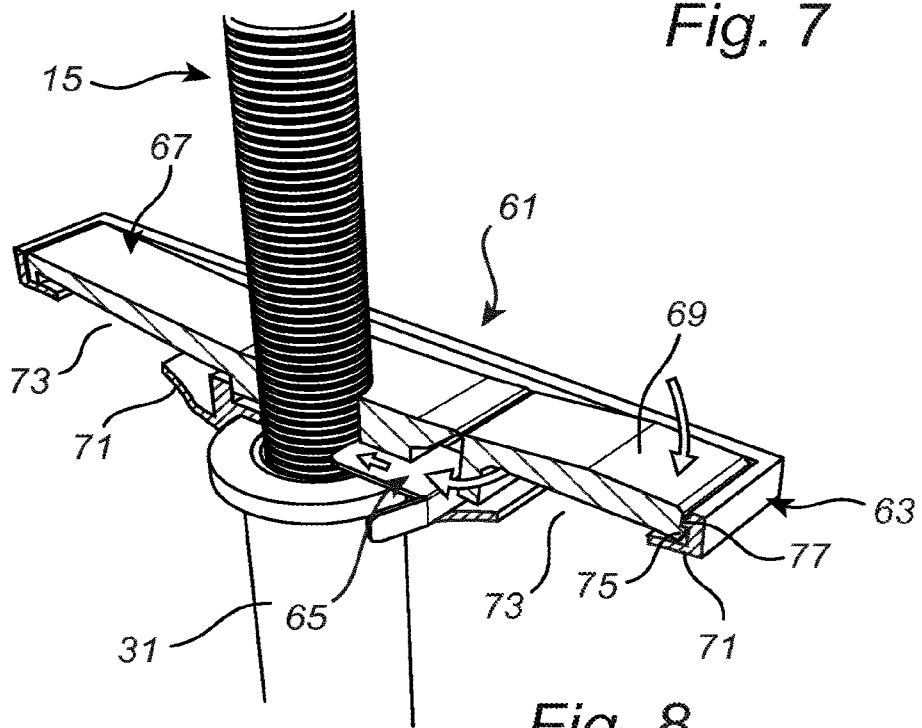
FIG. 8 is a sectional view of a syringe according to an embodiment of the present invention.

The FIGS. 1 to 7 show embodiments where the finger supporting surfaces 13 are provided at the lower side 11, and where they are preventing any access to the activation member 7 from the lower side 11. However according to another embodiment of the finger grip 61, as shown in FIG. 8, the finger grip comprises a body 63, an engagement member 65, and an activation member 67, the finger supporting surfaces 71 that are partially open, i.e. provided with holes 73, towards the activation member 67 such that the moving portion 69 of the activation member 67 can be forced to assume the inactive position again. This would typically require a certain amount of force in order to open the snap-in lock formed by the protrusions 75, 77, such that an unintentional inactivation of the engagement member 65 is prevented. This allows a user to switch between the active and the inactive position as desired while still preventing unintentional inactivation.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope of the claims.

The injection of crosslinked or non-crosslinked hyaluronic acid gels has been mentioned as a possible area of use for the device according to the invention. The hyaluronic acid gel is useful as a medical device, e.g. a dermal filler, for cosmetic use. It may also be useful in medical surgery, e.g. in eye surgery, joint surgery and medical cosmetic surgery or as a medicament, e.g. for treatment of joint disease. Naturally, it is possible to use the device according to the present invention with other liquid compositions, and preferably gel compositions, such as hydrogels. The device is also useful for injecting other types of dermal fillers than hyaluronic acid, e.g. collagen, calcium hydroxyl apatite, poly-L-lactic acid (PLLA), other polysaccharides and polymethylmethacrylate (PMMA). Furthermore, the device is useful for injecting liquid compositions comprising active substances and/or bioactive agents, such as local anesthetics, cicatrizants, antioxidants, botulinum toxin insulin or growth hormones. A preferred liquid composition of this type is a gel composition with a hyaluronic acid gel carrier and an active substance and/or a bioactive agent, e.g. a local anesthetic or a cicatrizant, such as dextranomer beads.

The invention claimed is:

1. A finger grip configured to connect to a syringe having a barrel, a plunger, and a plunger rod to drive the plunger, the finger grip comprising:
    a body having a lower side and an upper side, the lower side comprising at least one finger supporting surface to support one or more digits of a user;
    an engager movable between a first position where the engager is arranged not to contact the plunger rod and a second position where the engager is arranged to contact a surface of the plunger rod to provide feedback to the user; and
    an activator comprising a fixed part attached to the body and a movable part operable to move the engager between the first position and the second position, wherein the fixed part and the movable part are joined to each other by a pivotable joint,
    wherein the activator and the body comprise at least one concentric opening through which the plunger rod of the syringe is passable.

2. The finger grip of claim 1, wherein the activator is accessible from the upper side of the body.

3. The finger grip of claim 1, wherein the body is configured to impede access to the activator from the lower side of the body.

4. The finger grip of claim 1, wherein the fixed part and the movable part are at least partially disposed on opposite sides of the at least one concentric opening.

5. The finger grip of claim 1, wherein the engager comprises a metal material.

6. The finger grip of claim 1, wherein the engager comprises a tab having a planar tab portion with wing portions extending therefrom, and the activator comprises a planar activator portion.

7. The finger grip of claim 1, wherein the upper side of the body defines a frame arranged to surround the plunger rod and at least a part of an outer perimeter of the activator.

8. A finger grip configured to connect to a syringe having a barrel, a plunger, and a plunger rod to drive the plunger, the finger grip comprising:
    an engager movable between a first position where the engager is arranged not to contact the plunger rod and a second position where the engager is arranged to contact a surface of the plunger rod to provide feedback to a user;
    an activator operable to move the engager between the first position and the second position; and
    a body having a lower side and an upper side, the lower side comprising at least one finger supporting surface to support one or more digits of the user, the upper side defining a frame arranged to surround the plunger rod,
    wherein the frame and the activator comprise mating connectors that effectuate a snap-fit between the frame and the activator.

9. The finger grip of claim 8, wherein the mating connectors are disposed on an inner surface of the frame and an outer surface of the activator and secure the activator to the body.

10. The finger grip of claim 9, wherein the engager comprises a biasing member configured to bias the engager towards the first position.

11. The finger grip of claim 8, wherein an upper activator surface of the activator is flush with an upper frame surface of the frame when the engager is in the first position.

12. The finger grip of claim 8, wherein an upper activator surface of the activator is depressed relative to an upper frame surface of the frame when the engager is in the second position.

13. The finger grip of claim 9, further comprising a recess provided in the body and arranged to receive an end flange of the barrel.

14. A syringe including:
    a barrel;
    a plunger;
    a plunger rod configured to drive the plunger; and
    a finger grip comprising:
    a body having a lower side and an upper side, the lower side comprising at least one finger supporting surface to support one or more digits of a user;
    an engager movable between a first position where the engager is arranged not to contact the plunger rod and a second position where the engager is arranged to contact a surface of the plunger rod to provide feedback to the user; and
    an activator operable to move the engager between the first position and the second position,
    wherein the activator and the body comprise at least one concentric opening through which the plunger rod is passable.

15. The syringe of claim 14, wherein the body is configured to impede access to the activator from the lower side of the body.

16. The syringe of claim 14, wherein the activator comprises a fixed part attached to the body and a movable part disposed to move the engager, and wherein the fixed part and the movable part are joined to each other by a pivotable joint.

17. The syringe of claim 14, wherein the engager comprises a biasing member configured to bias the engager towards the first position.

18. The syringe of claim 14, wherein the upper side of the body defines a frame arranged to surround the plunger rod and at least a part of an outer perimeter of the activator.

19. The syringe of claim 18, wherein the frame includes a protrusion configured to prevent the activator from moving the engager from the second position to the first position.

20. A finger grip configured to connect to a syringe having a barrel, a plunger, and a plunger rod to drive the plunger, the finger grip comprising:
- a body having a lower side and an upper side, the lower side comprising at least one finger supporting surface to support one or more digits of a user;
- an engager movable between a first position where the engager is arranged not to contact the plunger rod and a second position where the engager is arranged to contact a surface of the plunger rod to provide feedback to the user; and
- an activator comprising a fixed part attached to the body and a movable part operable to move the engager between the first position and the second position, wherein the fixed part and the movable part are joined to each other by a pivotable joint,
- wherein the engager comprises a tab having a planar tab portion with wing portions extending therefrom, and the activator comprises a planar activator portion.

* * * * *